(12) United States Patent
Williams et al.

(10) Patent No.: US 12,082,835 B2
(45) Date of Patent: Sep. 10, 2024

(54) SURGICAL DEVICE INCLUDING TWO-CABLE HEMISPHERICAL GRASPER

(71) Applicant: Covidien LP, Mansfield, MA (US)

(72) Inventors: Justin Williams, Southbury, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 710 days.

(21) Appl. No.: 17/157,339

(22) Filed: Jan. 25, 2021

(65) Prior Publication Data

US 2021/0298779 A1    Sep. 30, 2021

Related U.S. Application Data

(60) Provisional application No. 62/994,479, filed on Mar. 25, 2020.

(51) Int. Cl.
*A61B 17/29* (2006.01)
*A61B 17/00* (2006.01)

(52) U.S. Cl.
CPC ...... *A61B 17/2909* (2013.01); *A61B 2017/00296* (2013.01); *A61B 2017/00367* (2013.01); *A61B 2017/2919* (2013.01); *A61B 2017/2937* (2013.01); *A61B 2017/2947* (2013.01)

(58) Field of Classification Search
CPC ...... A61B 17/2909; A61B 2017/00296; A61B 2017/00367; A61B 2017/2919; A61B 2017/2937; A61B 2017/2947; A61B 34/71; A61B 2017/00323; A61B 2017/2927; A61B 17/29
See application file for complete search history.

(56) References Cited

U.S. PATENT DOCUMENTS

| | | | |
|---|---|---|---|
| 7,879,070 B2 | 2/2011 | Ortiz et al. | |
| 8,062,306 B2 | 11/2011 | Nobis et al. | |
| 2002/0156497 A1* | 10/2002 | Nagase | A61B 17/062 606/205 |
| 2010/0011900 A1 | 1/2010 | Burbank | |
| 2010/0298864 A1 | 11/2010 | Castro | |
| 2013/0158593 A1 | 6/2013 | Kiapour et al. | |
| 2015/0313676 A1 | 11/2015 | Deodhar | |

(Continued)

FOREIGN PATENT DOCUMENTS

| | | |
|---|---|---|
| EP | 3205272 A1 | 8/2017 |
| EP | 3459473 A1 | 3/2019 |

(Continued)

OTHER PUBLICATIONS

Extended European Search Report issued in European Patent Application No. 21165312.6, dated Jul. 26, 2021.

(Continued)

*Primary Examiner* — Kathleen S Holwerda
*Assistant Examiner* — Daniel Icet
(74) *Attorney, Agent, or Firm* — Draft Masters PLLC

(57) ABSTRACT

A surgical grasper includes an articulation assembly configured to enable a tool assembly to pivot in a first plane and articulate in a second plane orthogonal to the first plane. The surgical grasper eliminates the center line pivot joint used in conventional articulation mechanism, which, in turn, enables use of thicker cable that provides greater clamping force of first and second jaws of the tool assembly.

18 Claims, 8 Drawing Sheets

(56) References Cited

U.S. PATENT DOCUMENTS

2015/0342585 A1* 12/2015 Steege ............... A61B 17/3201
606/1
2016/0287279 A1   10/2016 Bovay et al.
2017/0224332 A1*  8/2017 Hunter ................ A61B 17/105

FOREIGN PATENT DOCUMENTS

| JP | 2005103285 A | 4/2005 |
|----|--------------|--------|
| WO | 2016110720 A1 | 7/2016 |
| WO | 2019118334 A1 | 6/2019 |
| WO | 2019173267 A1 | 9/2019 |

OTHER PUBLICATIONS

European Office Action dated Jan. 27, 2023, issued in corresponding EP Appln. No. 21164458, 4 pages.

\* cited by examiner

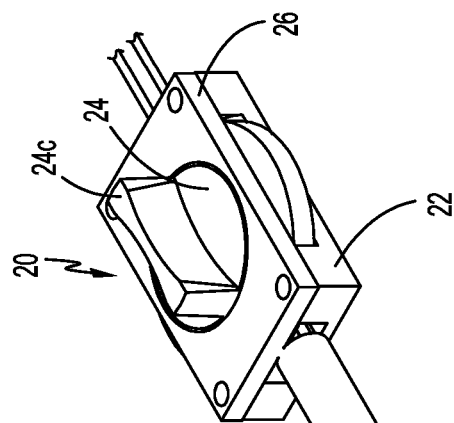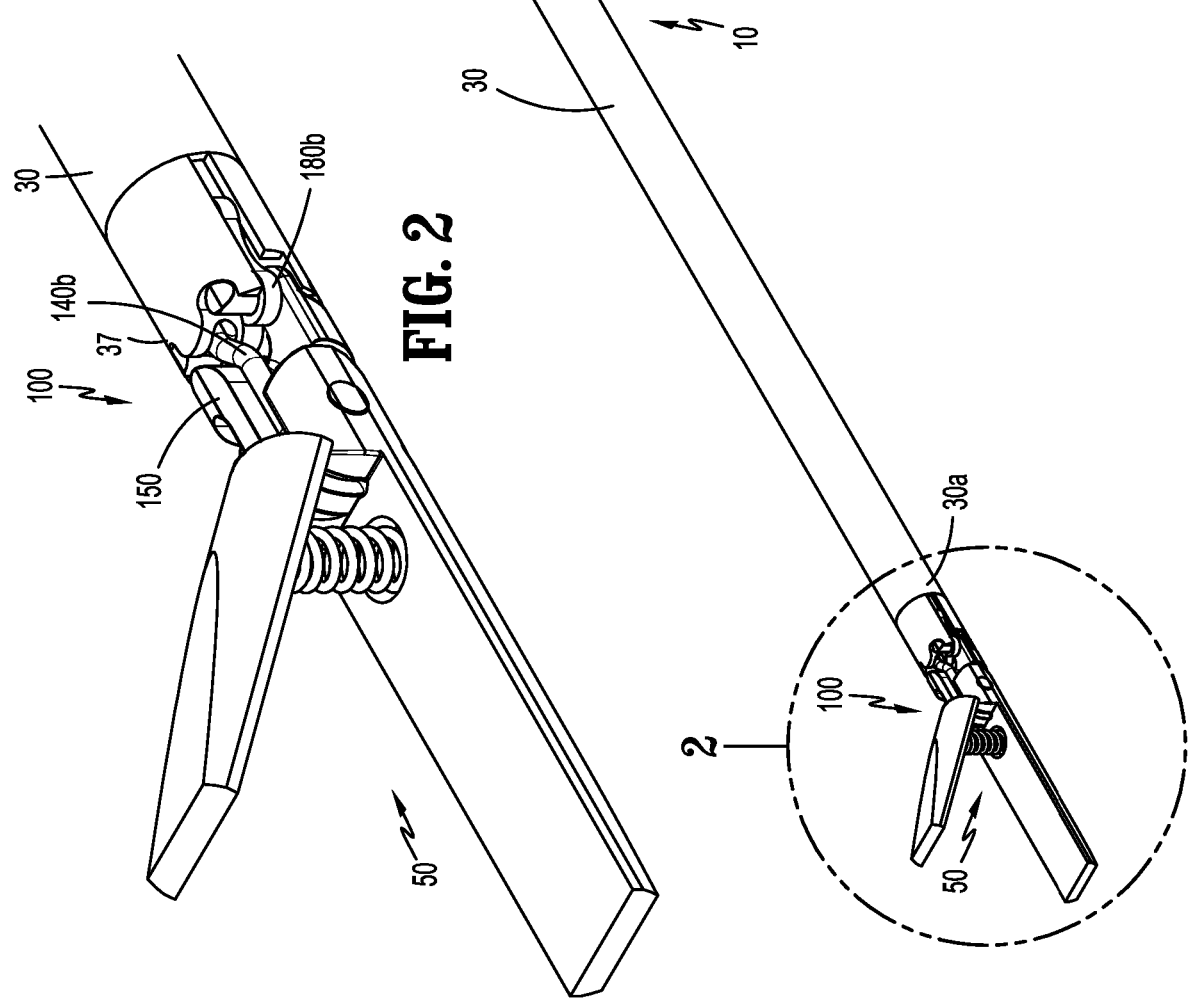

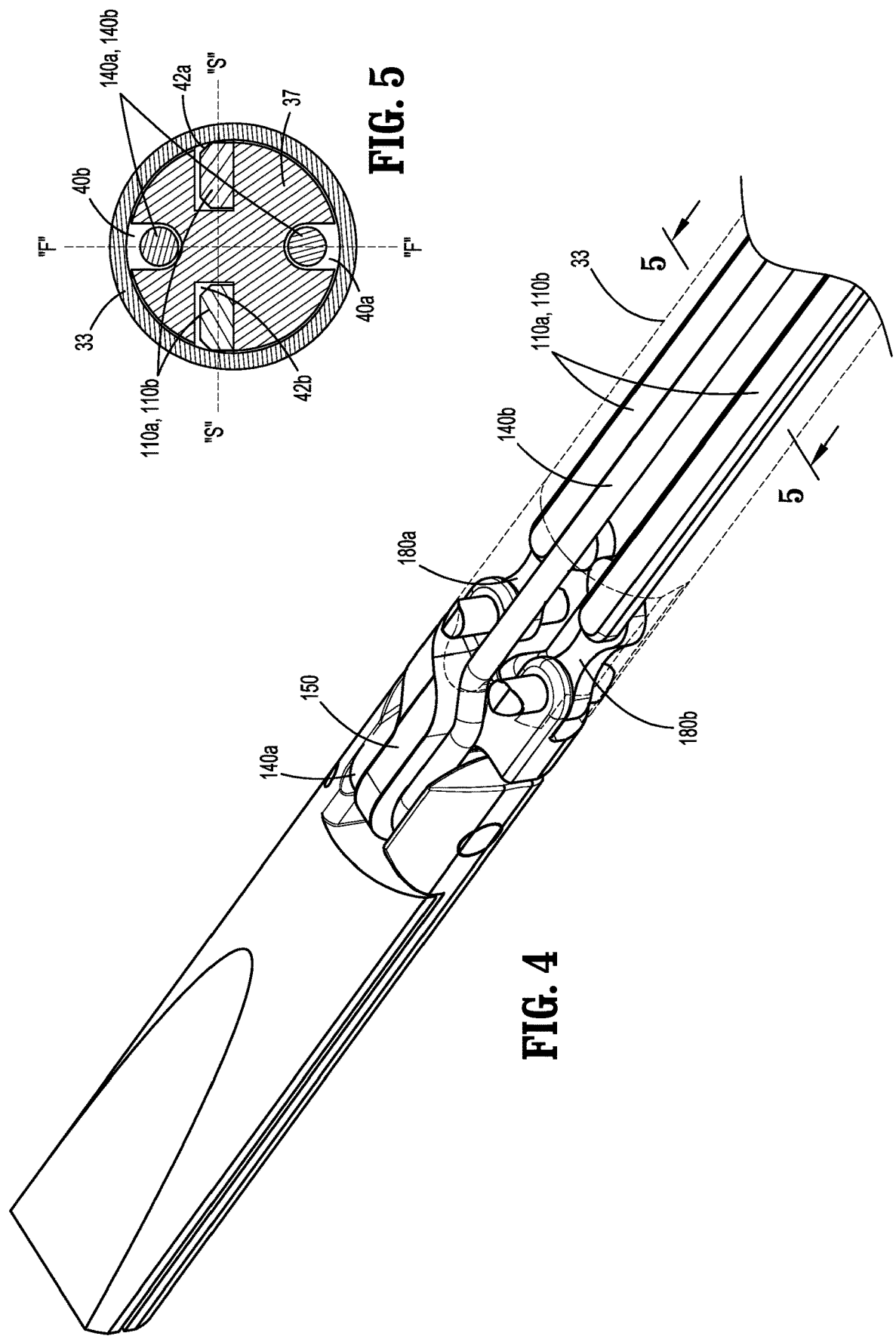

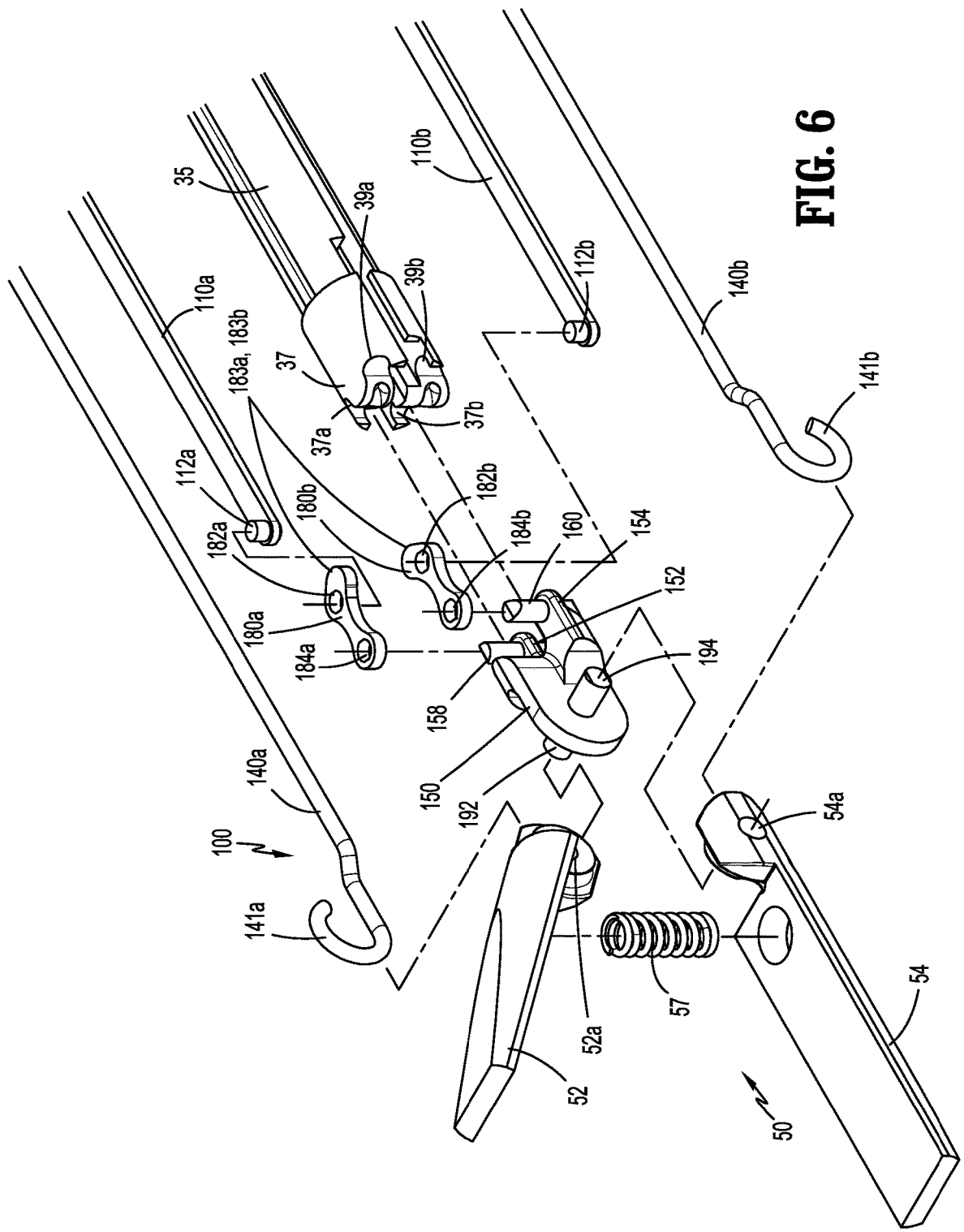

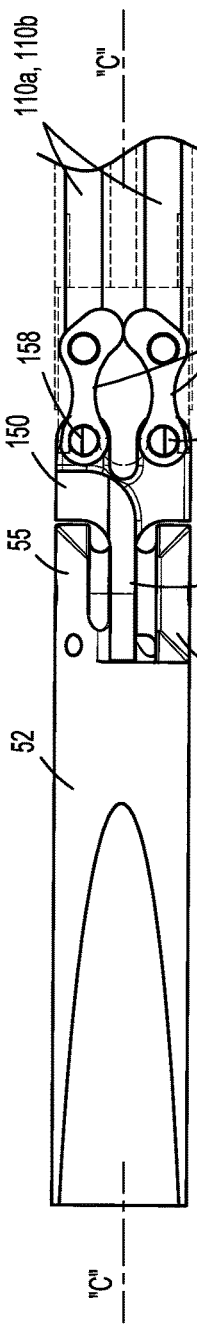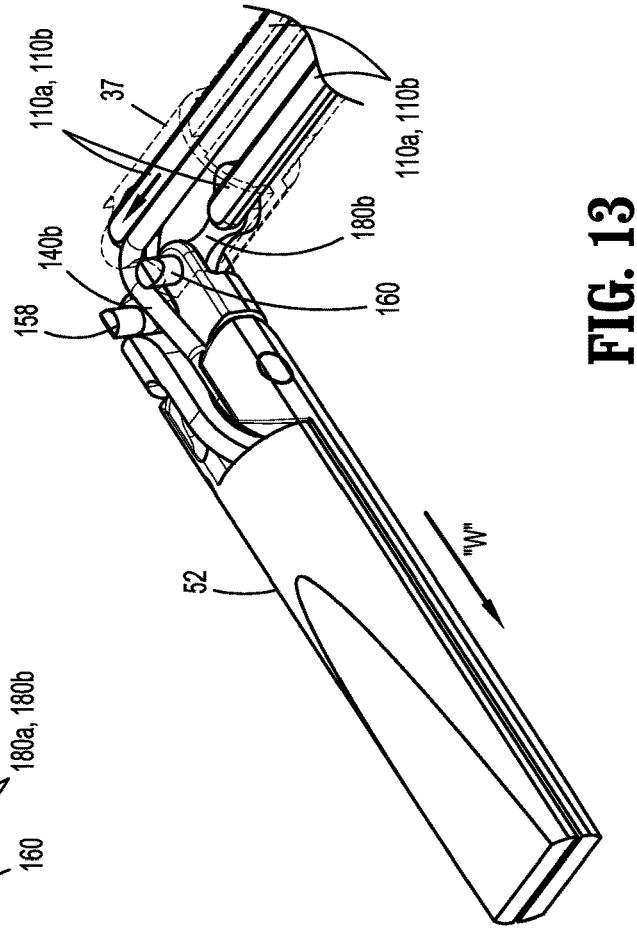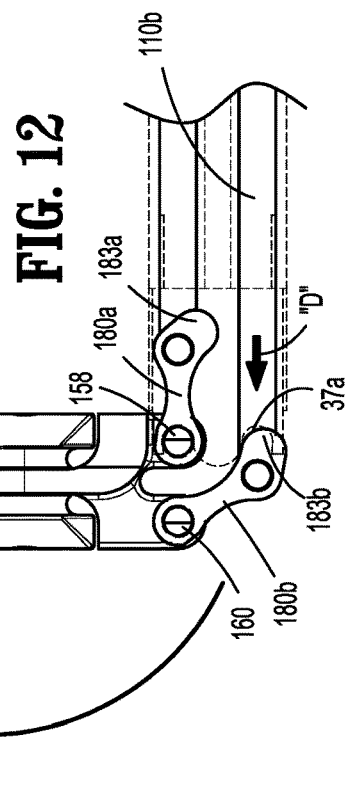

SURGICAL DEVICE INCLUDING TWO-CABLE HEMISPHERICAL GRASPER

CROSS-REFERENCE TO RELATED APPLICATIONS

This application claims the benefit of and priority to U.S. Provisional Patent Application Ser. No. 62/994,479, filed Mar. 25, 2020, the disclosure of which is incorporated by reference herein in its entirety.

TECHNICAL FIELD

This disclosure relates to surgical devices for performing endoscopic surgical procedures. More specifically, this disclosure relates to a surgical device including a two-cable hemispherical grasper.

BACKGROUND

During laparoscopic or endoscopic surgical procedures, access to a surgical site is achieved through a small incision or through a narrow cannula inserted through a small opening in a patient. Because of limited area to access the surgical site, many endoscopic surgical devices include mechanisms for articulating the tool assembly of the device. Typically, the articulation mechanism is controlled by an actuator which has to be manipulated by a surgeon to properly orient the tool assembly in relation to tissue to be treated.

SUMMARY

In accordance with this disclosure, a surgical grasper includes a tool assembly and an articulation assembly. The tool assembly includes first and second jaws defining respective first and second bores. The first and second jaws are transitionable between an approximated configuration and a spaced apart configuration. The articulation assembly includes first and second articulation members, first and second actuation members, an articulation joint, and first and second linkage members. Portions of the first and second actuation members are coupled to the respective first and second jaws such that axial displacement of the first actuation member rotates the first and second jaws in a first direction and axial displacement of the second actuation member rotates the first and second jaws in a second direction. The articulation joint includes first and second protrusions extending laterally in opposite directions and configured to be received through the respective first and second bores of the first and second jaws, and first and second pegs extending orthogonal to the first and second protrusions. The first and second linkage members interconnect the first and second articulation members to the respective first and second pegs such that axial displacement of the first articulation cable pivots the tool assembly about the second peg, and axial displacement of the second articulation cable pivots the tool assembly about the first peg.

In an aspect, the first and second jaws of the tool assembly may be pivotable in a first plane.

In another aspect, the first and second jaws may be articulatable in a second plane orthogonal to the first plane.

In yet another aspect, the tool assembly may further include a biasing member to bias the first and second jaws towards the spaced apart configuration.

In still yet another aspect, axial displacement of the first and second actuation members may transition the first and second jaws to the approximated configuration.

In an aspect, the portions of the first and second actuation members may partially surround the respective first and second bores of the first and second jaws in opposite directions.

In another aspect, the first and second linkage members may define respective proximal bores. The proximal bores may be configured to receive bosses of the respective first and second articulation members.

In yet another aspect, the first and second linkage members may include respective extension portions extending radially inward from the respective proximal bores.

In still yet another aspect, the first and second linkage members may define respective distal bores configured to receive the respective first and second pegs of the articulation members. In an aspect, the first and second articulation members may be laterally spaced apart.

In another aspect, the first and second actuation members may define a first axis orthogonal to a second axis defined by the first and second articulation members.

In yet another aspect, the first and second actuation members may be formed of flexible members.

In still yet another aspect, the first and second jaws may include respective first and second neck portions. The articulation joint may include a base member interposed between the first and second neck portions.

In another aspect, the first and second protrusions of the articulation joint may extend from the base member in opposite directions.

In accordance with another aspect of the disclosure, an articulation assembly for use with a surgical device includes first and second articulation members, first and second actuation members, an articulation joint, and first and second linkage members. The first and second actuation members are coupled to respective first and second jaws of a surgical device such that axial displacement of the first actuation member pivots the first and second jaws in a first direction and axial displacement of the second actuation member pivots the first and second jaws in the second direction opposite of the first direction. The articulation joint includes first and second protrusions extending laterally in opposite directions and configured to pivotably support the respective first and second jaws, and first and second pegs laterally spaced apart and extending orthogonal to the first and second protrusions. The first and second linkage members interconnect the first and second articulation members to the respective first and second pegs such that axial displacement of the first articulation cable pivots the first and second jaws about the second peg, and axial displacement of the second articulation cable pivots the first and second jaws about the first peg.

In an aspect, the articulation assembly further includes a mount configured to slidably support the first and second linkage members, and pivotably engaging the first and second pegs.

In another aspect, the mount may define laterally spaced apart slots configured to slidably receive the respective first and second linkage members therein.

In yet another aspect, the mount may define grooves laterally spaced apart. The grooves may be configured to pivotably support the respective first and second pegs of the articulation joint.

In still yet another aspect, the mount may define longitudinal bores spaced apart from a central axis defined by the mount. The longitudinal bores may be configured to slidably receive the respective first and second actuation members.

In still yet another aspect, the first and second actuation members may include respective distal portions bendable to form an arcuate profile.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

FIG. 1 is a perspective view of an endoscopic surgical grasper in accordance with this disclosure;

FIG. 2 is an enlarged perspective view of the indicated area of detail of FIG. 1;

FIG. 4 is a partial perspective view of the endoscopic surgical grasper of FIG. 1 with an outer tube of an elongate shaft removed;

FIG. 5 is an end cross-sectional view take along section line 5-5 of FIG. 4;

FIG. 6 is an enlarged exploded perspective view of the indicated area of detail of FIG. 3;

FIG. 11 is a partial top view of the endoscopic surgical grasper of FIG. 1, illustrating the tool assembly in a straight configuration;

FIG. 12 is a top view of the endoscopic surgical grasper of FIG. 11, illustrating articulation of the tool assembly in a first direction;

FIG. 13 is a top view of the endoscopic surgical grasper of FIG. 11, illustrating articulation of the tool assembly in a second direction.

DETAILED DESCRIPTION

Figure 3:
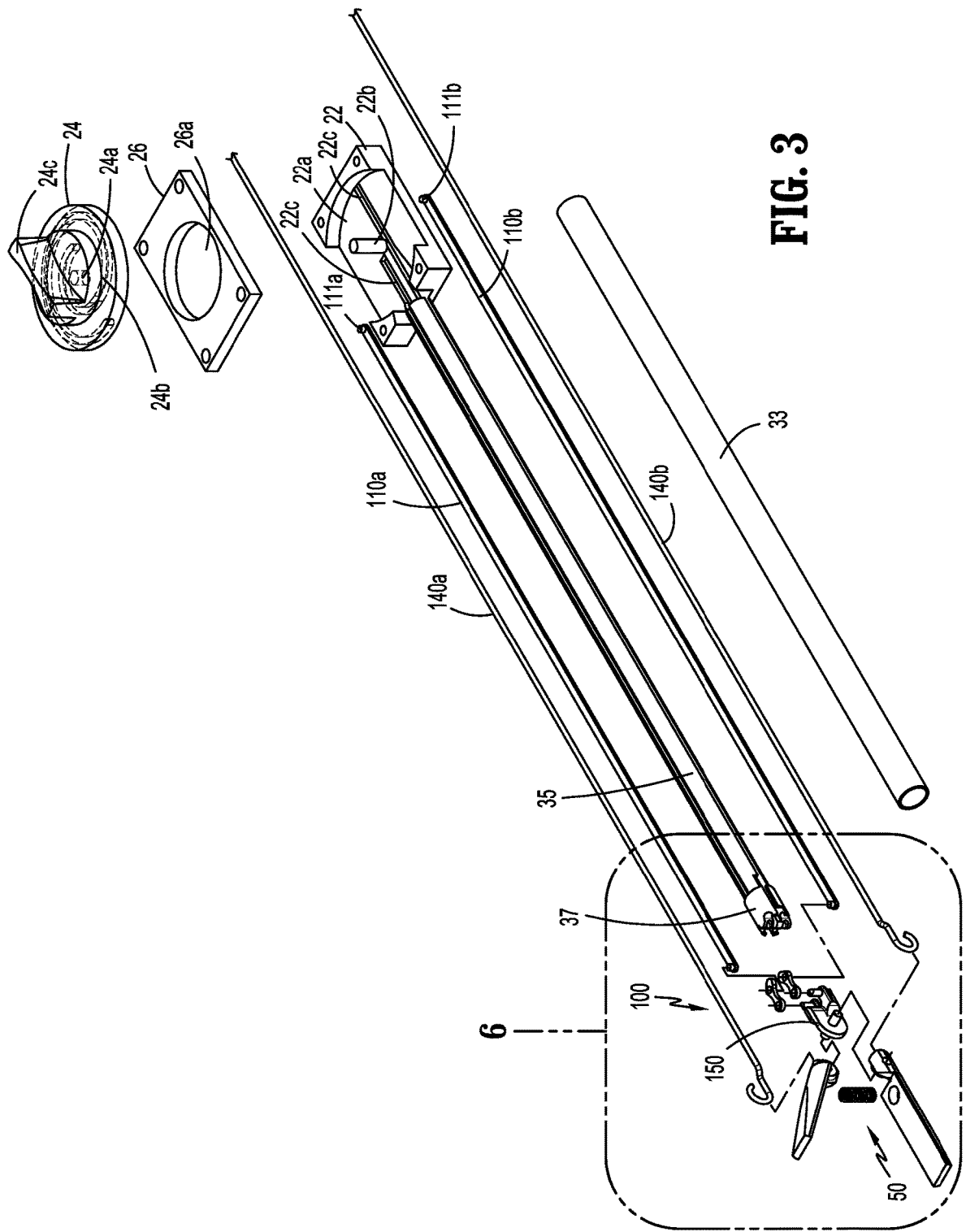
FIG. 3 is an exploded perspective view of the endoscopic surgical grasper of FIG. 1 with parts separated.

The endoscopic surgical device disclosed herein is described in detail with reference to the drawings, in which like reference numerals designate identical or corresponding elements in each of the several views.

As used herein, the term "distal" refers to the portion that is being described which is further from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Non-limiting examples of endoscopic surgical devices which may include articulation joints according to the disclosure include manual, mechanical and/or electromechanical surgical tack appliers, surgical clip appliers, surgical staplers, surgical stitching devices and the like.

In FIGS. 1 and 2, an exemplary articulation assembly for use with endoscopic surgical device, in the form of an endoscopic surgical grasper 10, is shown generally as 100. The articulation assembly 100 is configured to maximize clamping force while minimizing the size of an entrance opening in a patient. The endoscopic surgical grasper 10 includes a handle assembly 20, an endoscopic shaft 30 extending from the handle assembly 20, the articulation assembly 100 supported at a distal end portion 30a of the endoscopic shaft 30, and a tool assembly 50 coupled to the articulation assembly 100. The tool assembly 50 is configured to pivot in a first plane and articulate in a second plane orthogonal to the first plane, thereby enabling the tool assembly 50 for a full hemispherical reach within the surgical site.

FIGS. 3-5 illustrate the endoscopic shaft 30 including an outer tube 33 and an inner support 35 slidably supporting first and second articulation members 110a, 110b. In particular, the inner support 35 includes a distal mount 37 defining bores 40a, 40b that are diametrically opposed to each other and configured to receive respective first and second actuation members 140a, 140b. The distal mount 37 includes slots 42a, 42b that are diametrically opposed to each other and configured to slidably receive the respective first and second articulation members 110a, 110b. In particular, the bores 40a, 40b are radially spaced about from a central longitudinal axis "C" (FIG. 10) and define a first axis "F". The slots 42a, 42b are also laterally spaced apart from each other and define a second axis "S". The first and second axes "F", "S" may be orthogonal to each other. FIG. 6 shows the distal mount 37 defining a first pair of grooves 37a, 37b on a first lateral side of the distal mount 37, and a second pair of grooves 39a, 39b on a second lateral side of the distal mount 37. The grooves 37a, 37b are in registration with each other, and the grooves 39a, 39b are in registration with each other. In particular, the grooves 37a, 39a laterally oppose each other, and grooves 37b, 39b laterally oppose each other. The first and second pairs of grooves 37a, 37b, 39a, 39b are configured to engage the articulation joint 150 as discussed below.

Figure 10:
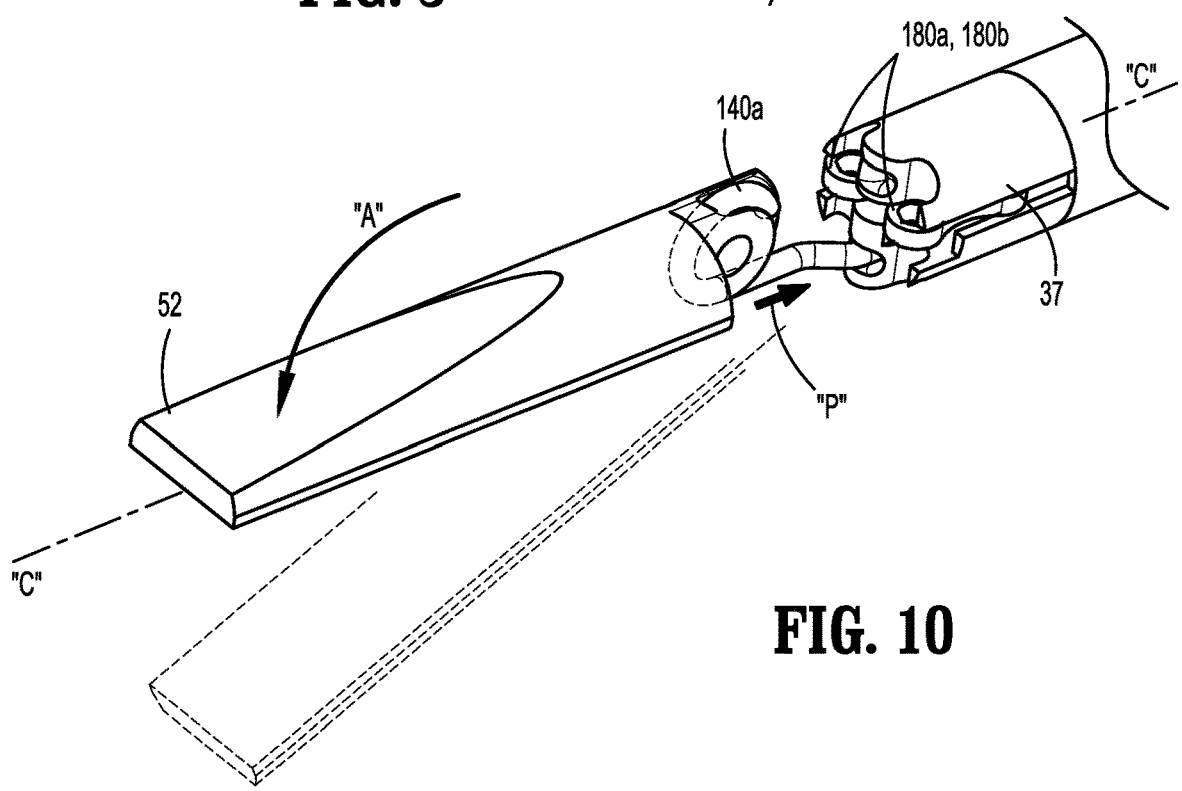
FIG. 10 is a partial perspective view of the endoscopic surgical grasper of FIG. 1 with linkage members of the articulation assembly removed.

FIGS. 4-6 show the articulation assembly 100 including the first and second articulation members 110a, 110b, the first and second actuation members 140a, 140b, an articulation joint 150, and first and second linkage members 180a, 180b. The first and second articulation members 110a, 110b are slidably supported within the inner support 35. In particular, the first and second articulation members 110a, 110b include respective first and second bosses 112a, 112b configured to engage respective first and second proximal bores 182a, 182b of the corresponding first and second linkage members 180a, 180b. The first and second linkage members 180a, 180b laterally oppose each other. The first linkage member 180a defines proximal and distal bores 182a, 184a on respective opposite end portions thereof. Further, the first linkage member 180a includes an extension portion 183a extending radially inward towards the central longitudinal axis "C" (FIG. 10). The second linkage member 180b is a mirror image of the first linkage member 180a. The second linkage member 180b defines proximal and distal bores 182b, 184b on respective opposite end portions thereof. In particular, the second linkage member 180b includes an extension portion 183b extending radially inward towards the central longitudinal axis "C".

Figure 7:
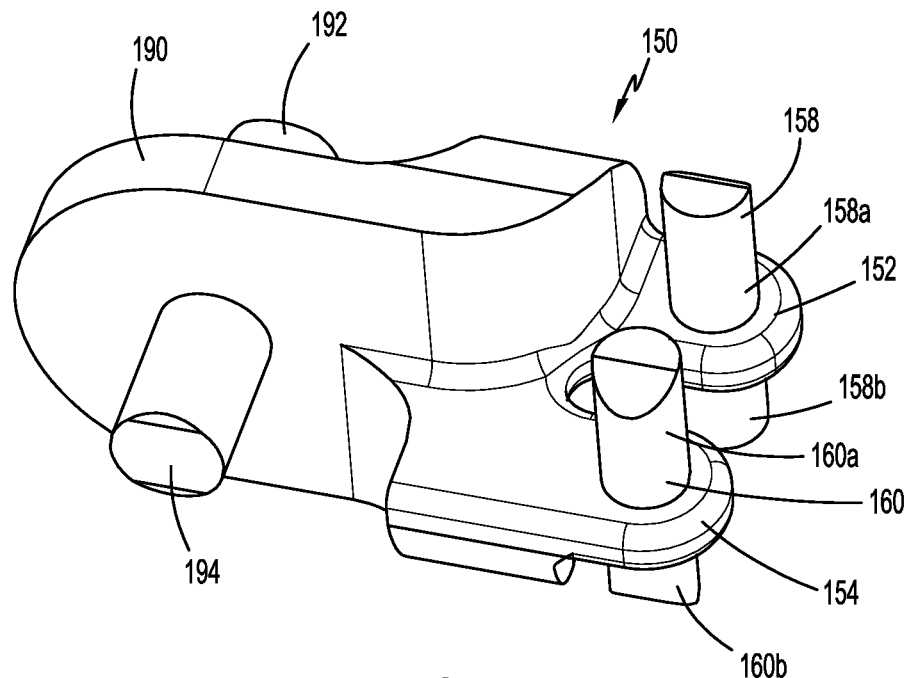
FIG. 7 is a perspective view of an articulation joint of an articulation assembly of FIG. 1.

FIGS. 6 and 7 show the articulation joint 150 operatively associated with the first and second jaws 52, 54 of the tool assembly 50 and the first and second linkage members 180a, 180b. In particular, the articulation joint 150 includes laterally opposing first and second supports 152, 154. The first and second supports 152, 154 include respective first and second pegs 158, 160. The first peg 158 includes first and second portions 158a, 158b extending in opposite directions orthogonal to the central longitudinal axis "C". Similarly, the second peg 160 includes first and second portions 160a, 160b extending in opposite directions orthogonal to the central longitudinal axis "C". The first and second portions 158a, 158b of the first peg 158 are configured to pivotably engage the respective grooves 37a, 37b of the distal mount 37 of the endoscopic shaft 30. Similarly, the first and second portions 160a, 160b of the second peg 160 are configured to pivotably engage the respective grooves 39a, 39b of the distal mount 37. In addition, the first portions 158a, 160a of the respective first and second pegs 158, 160 are received through the distal bores 184a, 184b of the respective first and second linkage members 180a, 180b. In addition, the articulation joint 150 further includes a base member 190 and first and second lateral protrusions 192, 194 extending from the base member 190 in opposite directions. The first and second lateral protrusions 192, 194 are configured to extend through bores 52a, 54a of the respective first and second jaws 52, 54.

Figure 8:
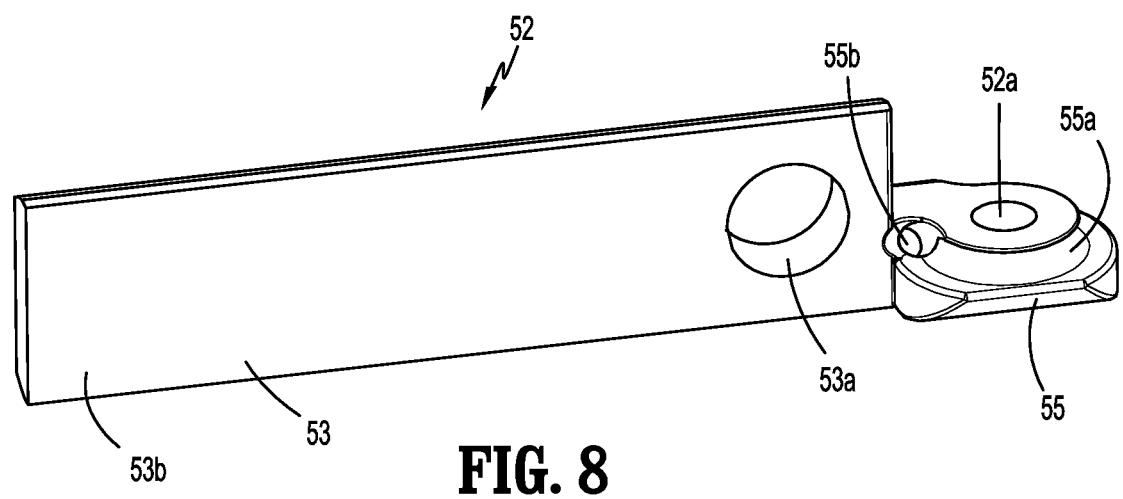
FIG. 8 is a jaw member of a tool assembly of the endoscopic surgical grasper of FIG. 1.

FIG. 8 illustrates the first jaw member 52. The second jaw member 54 is a mirror image of the first jaw member 52. In the interest of brevity, only the first jaw member 52 is shown and described. The first jaw member 52 includes a grasping portion 53 and a neck portion 55 extending proximally from the grasping portion 53. The grasping portion 53 includes, e.g., a substantially planar, surface 53b configured to engage, e.g., tissue. The grasping portion 53 defines a cavity 53a configured to secure a portion of a biasing member 57 (FIG. 6) therein. In particular, the neck portion 55 defines the bore 52a configured to receive the first lateral protrusion 192 of the articulation joint 150. For example, the bore 52a may be concentrically defined with respect to the neck portion 55. In addition, the neck portion 55 further defines a groove 55a about the bore 52a to receive a portion of the actuation member 140, and a hole 55b configured fixedly receive a distal end portion 141a (FIG. 6) of the first actuation member 140a to secure the distal end portion 141a thereto.

Figure 9:
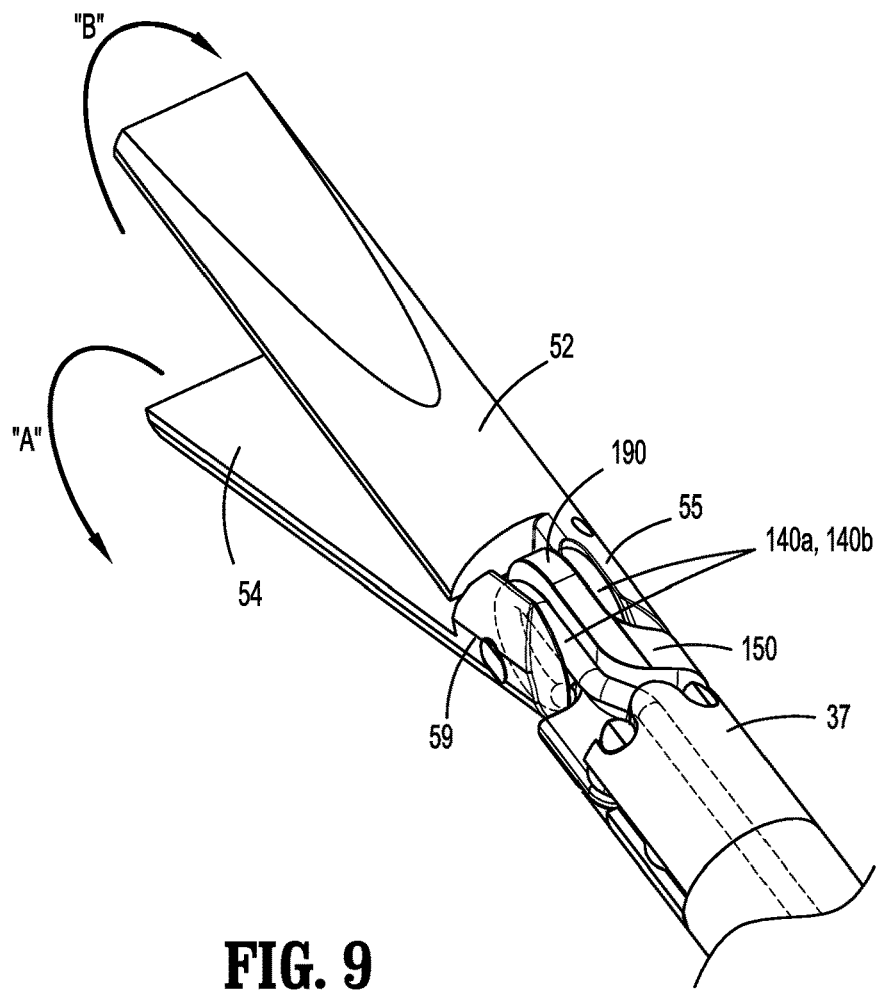
FIG. 9 is a partial perspective view of the endoscopic surgical grasper, illustrating the actuation members.

FIGS. 9 and 10 show the first and second jaws 52, 54 operatively coupled to the articulation joint 150. The neck portions 55, 59 of the respective first and second jaws 52, 54 are disposed on opposing sides of the base member 190 of the articulation joint 150. In particular, the respective first and second articulation members 140a, 140b are interposed between the base member 190 and the corresponding neck portion 55, 59. As discussed hereinabove, the first and second lateral protrusions 192, 194 of the articulation joint 150 are received in the bores 52a, 54a of the respective first and second jaws 52, 54.

In particular, the distal end portions 141a, 141b of the respective first and second actuation members 140a, 140b are at least partially wrapped around the respective neck portions 55, 59 via grooves 55a (groove for the neck portion 59 not shown) in opposite directions. Under such a configuration, retraction of the first or second actuation member 140a, 140b (in the direction of an arrow "P") pivots the first and second jaws in opposite directions. For example, when the first actuation member 140a is retracted, the first and second jaws 52, 54 rotate in the direction of an arrow "A" and when the second actuation member 140b is retracted, the first and second jaws 52, 54 rotate in the direction of an arrow "B". As discussed above, the biasing member 57 biases the first and second jaws 52, 54 toward the spaced part configuration, and thus, rotation of one of the first and second jaws 52, 54 causes rotation of the other one of the first and second jaws 52, 54 in the spaced apart configuration. Under such a configuration, when both the first and second actuation members 140a, 140b are retracted, the first and second jaws 52, 54 are transitioned to the approximated configuration to clamp, e.g., tissue, therebetween.

FIG. 11 illustrates the first and second articulation members 110a, 110b operatively coupled to the articulation joint 150. Through the use of the first and second articulation members 110, the first and second jaws 52, 54 are laterally articulatable in the direction of an arrow "W" (FIG. 13) and in the direction of an arrow "R" (FIG. 12) from a straight configuration in which the first and second jaws 52, 54 are aligned with the central longitudinal axis "C-C". In the straight configuration, the first peg 158 is received in the first pair of grooves 37a, 37b, and the second peg 160 is received in the second pair of grooves 39a, 39b. Further, the extension portions 183a, 183b (FIG. 6) of the first and second linkage members 180a, 180b engage each other. However, when the first articulation member 110a is displaced in the direction of an arrow "D" (FIG. 12), the first peg 158 of the articulation member 150 is displaced from the first pair of grooves 37a, 37b and extends away from the distal mount 37 (FIG. 6) of the endoscopic shaft 30, as shown in FIG. 13. However, the extension portion 183a of the first linkage member 180a remains in the distal mount 37 to support the first linkage member 180a thereon. At this time, the second peg 160 of the articulation joint 150 remains in the second pair of grooves 39a, 39b of the distal mount 37 such that the first and second jaws 52, 54 pivot about the second peg 160, as shown in FIG. 13. Similarly, when the second articulation member 110b is displaced in the direction of an arrow "D", the second peg 160 of the articulation member 150 is displaced from the second pair of grooves 39a, 39b and extends away from the distal mount 37 (FIG. 6) of the endoscopic shaft 30. However, the extension portion 183b of the second linkage member 180b remains in the distal mount 37 to support the second linkage member 180b thereon. At this time, the first peg 158 of the articulation joint 150 remains in the first pair of grooves 37a, 37b such that the first and second jaws 52, 54 pivot about the first peg 158 as shown in FIG. 12.

Figure 14:
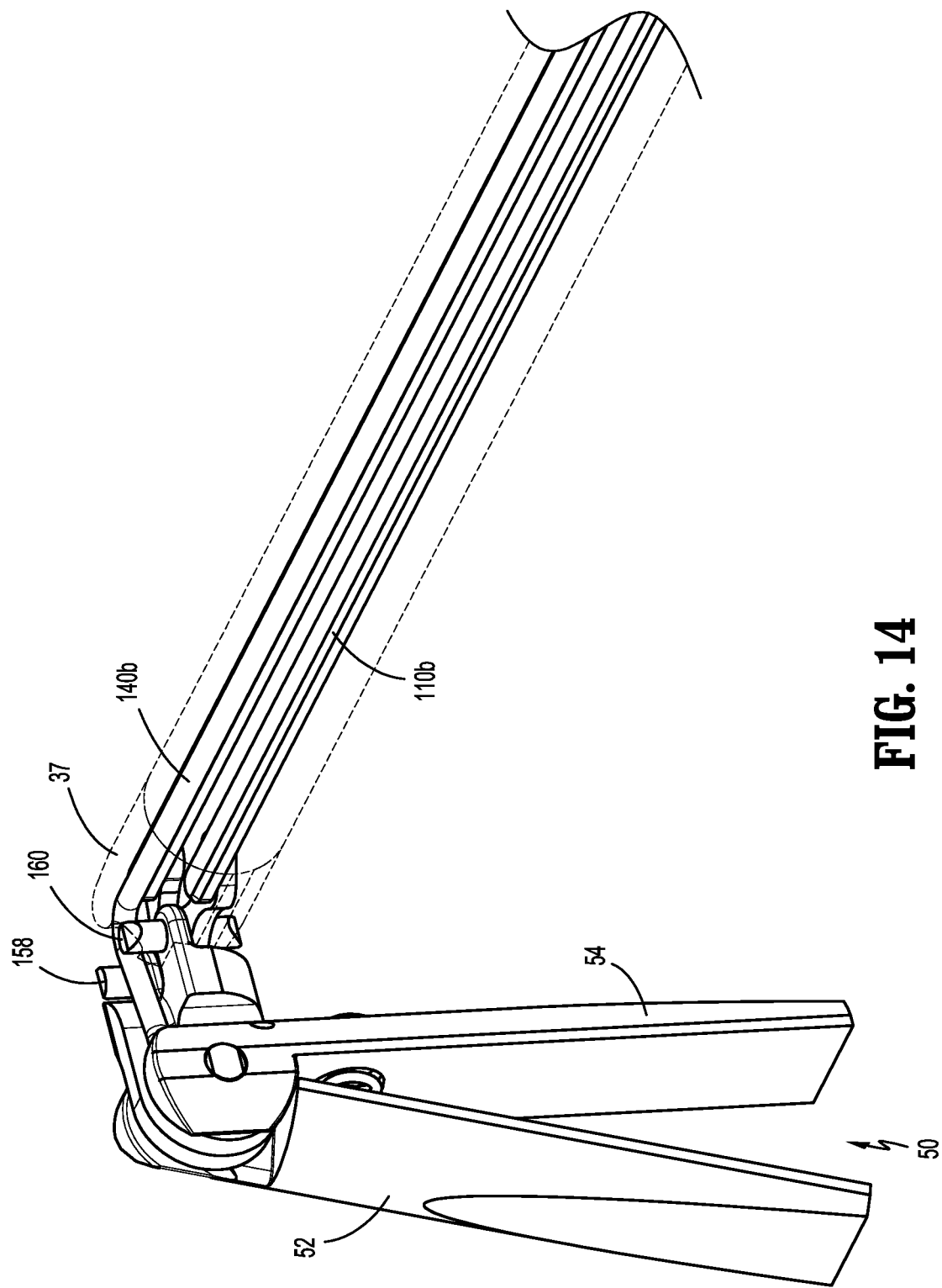
FIG. 14 is a perspective view of the endoscopic surgical grasper of FIG. 11, illustrating articulation and pivoting of the tool assembly.

Under such a configuration, by utilizing the first and second articulation members 110a, 110b and the first and second actuation members 140a, 140b, the tool assembly 50 may be pivoted in a first plane and articulated in a second plane orthogonal to the first plane. In this manner, the tool assembly 50 may be manipulated and have a full hemispherical reach within the surgical site as shown in FIG. 14. Furthermore, such a configuration eliminates the center line pivot joint used in a conventional articulation mechanism, which, in turn, enables use of thicker cable that provides greater clamping force of the first and second jaws 52, 54.

It is contemplated that while the articulation assembly 100 is shown for use with the endoscopic surgical grasper 10, the articulation assembly 100 may be configured for use with other surgical devices such as, e.g., surgical staplers or tack appliers.

FIGS. 1 and 3 illustrate a handle assembly 20 operatively coupled with the articulation members 110. The handle assembly 20 includes a base portion 22, a rotatable member 24, and a cover 26. The base portion 22 defines a circular recess 22a configured to rotatably receive the rotatable member 24 therein, and grooves 22c configured to slidably receive respective first and second articulation members 110a, 110b. The base portion 22 includes a protrusion 22b configured to be received in the hole 24a defined in the rotatable member 24 to rotatably support the rotatable member 24 thereon. The rotatable member 24 has an underside defining a coiled groove 24b about the hole 24a. The rotatable member 24 further includes a knob 24c configured to be gripped by a clinician to rotate the rotatable member 24. The cover 26 defines a bore 26a configured to receive the knob 24c of the rotatable member 24 therethrough. The cover 26 is positioned in superposed relation with the rotatable member 24 such that the rotatable member 24 is rotatably secured with the base portion 22. In particular, the proximal end portions of the first and second articulation members 110a, 110b include respective bosses 111a, 111b configured to cammingly engage the coiled groove 24b. The coiled groove 24b is configured to hold one of the first and second articulation members 110a, 110b back, while advancing the other first and second articulation members 110a, 110b when the knob 24c of the rotatable member 24 is rotated. In this manner, rotation of the knob 24c controls the articulation of the tool assembly 50 in the direction of arrows "R" (FIG. 12) and "W" (FIG. 13). However, it is contemplated that the first and second articulation members 110a, 110b may be coupled to an electro-mechanical device such as, e.g., an electrical motor, to effect articulation of the first and second jaws 52, 54. Furthermore, the first and second actuation members 140a, 140b may be mechanically operated by a trigger or an electro-mechanical device, as known by one skilled in the art to retract each of the first and second actuation members 140a, 140b alone or together to pivot or clamp the jaw members 52, 54, as discussed above. It is also envisioned that the articulation assembly 100 may be configured to connect to a robotic arm of a robotic surgical system to enable manipulation and control thereof.

In use, the endoscopic surgical grasper 10 is initially placed in the straight configuration and the first and second jaws 52, 54 are in the approximated configuration, in which, the first and second articulation members 140a, 140b are retracted in the direction of the arrow "P". At this time, the clinician may position the first and second jaws 52, 54 through an opening in tissue. Thereafter, the first and second articulation members 110a, 110b and/or the first and second actuation members 140a, 140b may be manipulated to pivot and/or articulate the first and second jaws 52, 54 to place the first and second jaws 52, 54 adjacent a target tissue. Thereafter, the endoscopic surgical grasper 10 may be actuated to grasp the desired object such as, e.g., tissue or mesh (not shown), as needed.

While specific instruments have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A surgical grasper comprising:
    a tool assembly including a first jaw and a second jaw defining a first bore and a second bore respectively, the first jaw and the second jaw transitionable between an approximated configuration and a spaced apart configuration; and
    an articulation assembly including:
        a first articulation member and a second articulation member;
        a first actuation member and a second actuation member, a distal portion of the first actuation member engaging a first groove of the first jaw and a distal portion of the second actuation member engaging a second groove of the second jaw such that axial displacement of the first actuation member rotates the first jaw and the second jaw in a first direction and axial displacement of the second actuation member rotates the first jaw and the second jaw in a second direction;
        an articulation joint including:
            a first protrusion and a second protrusion extending laterally in opposite directions and configured to be received through the first bore and the second bore of the first jaw and the second jaw respectively; and
            a first peg and a second peg extending orthogonal to the first protrusion and the second protrusion; and
            a first linkage member and a second linkage member interconnecting the first articulation member and the second articulation member to the first peg and the second peg respectively such that axial displacement of the first articulation member pivots the tool assembly about the second peg, and axial displacement of the second articulation member pivots the tool assembly about the first peg;
        wherein the first linkage member and the second linkage member define respective proximal bores, the proximal bores configured to receive bosses of the first articulation member and the second articulation member respectively.

2. The surgical grasper according to claim 1, wherein the first jaw and the second jaw of the tool assembly are pivotable in a first plane.

3. The surgical grasper according to claim 2, wherein the first jaw and the second jaw are articulatable in a second plane orthogonal to the first plane.

4. The surgical grasper according to claim 1, wherein the tool assembly further includes a biasing member to bias the first jaw and the second jaw towards the spaced apart configuration.

5. The surgical grasper according to claim 1, wherein axial displacement of the first actuation member and the second actuation member transitions the first jaw and the second jaw to the approximated configuration.

6. The surgical grasper according to claim 1, wherein distal portions of the first actuation member and the second actuation member partially surround the first bore and the second bore of the first jaw and the second jaw respectively in opposite directions.

7. The surgical grasper according to claim 1, wherein the first linkage member and the second linkage member include respective extension portions extending radially inward from the respective proximal bores.

8. The surgical grasper according to claim 1, wherein the first articulation member and the second articulation member are laterally spaced apart.

9. The surgical grasper according to claim 8, wherein the first actuation member and the second actuation member define a first axis orthogonal to a second axis defined by the first articulation member and the second articulation member.

10. The surgical grasper according to claim 1, wherein the first actuation member and the second actuation member are formed of flexible members.

11. The surgical grasper according to claim 1, wherein the first jaw and the second jaw include a first neck portion and a second neck portion respectively, the articulation joint including a base member interposed between the first neck portion and the second neck portion.

12. The surgical grasper according to claim 11, wherein the first protrusion and the second protrusion of the articulation joint extend from the base member in opposite directions.

13. A surgical grasper comprising:
a tool assembly including a first jaw and a second jaw defining a first bore and a second bore respectively, the first jaw and the second jaw transitionable between an approximated configuration and a spaced apart configuration; and
an articulation assembly including:
  a first articulation member and a second articulation member;
  a first actuation member and a second actuation member, a distal portion of the first actuation member engaging a first groove of the first jaw and a distal portion of the second actuation member engaging a second groove of the second jaw such that axial displacement of the first actuation member rotates the first jaw and the second jaw in a first direction and axial displacement of the second actuation member rotates the first jaw and the second jaw in a second direction;
  an articulation joint including:
    a first protrusion and a second protrusion extending laterally in opposite directions and configured to be received through the first bore and the second bore of the first jaw and the second jaw respectively; and
    a first peg and a second peg extending orthogonal to the first protrusion and the second protrusion; and
    a first linkage member and a second linkage member interconnecting the first articulation member and the second articulation member to the first peg and the second peg respectively such that axial displacement of the first articulation member pivots the tool assembly about the second peg, and axial displacement of the second articulation member pivots the tool assembly about the first peg;
  wherein the first linkage member and the second linkage member define respective distal bores configured to receive the first peg and the second peg of the articulation members, respectively.

14. An articulation assembly for use with a surgical device, the articulation assembly comprising:
  a first articulation member and a second articulation member;
  a first actuation member having a first hook and a second actuation member having a second hook, the first hook coupled to a first jaw of the surgical device and the second hook coupled to a second jaw of the surgical device such that axial displacement of the first actuation member pivots the first jaw and the second jaw in a first direction and axial displacement of the second actuation member pivots the first jaw and the second jaw in a second direction opposite of the first direction;
  an articulation joint including:
    a first protrusion and a second protrusion extending laterally in opposite directions and configured to pivotably support the first jaw and the second jaw respectively; and
    a first peg and a second peg laterally spaced apart and extending orthogonal to the first protrusion and the second protrusion; and
    a first linkage member and a second linkage member interconnecting the first articulation member and the second articulation member to the first peg and the second peg respectively such that axial displacement of the first articulation member pivots the first jaw and the second jaw about the second peg, and axial displacement of the second articulation member pivots the first jaw and the second jaw about the first peg; and
  a mount configured to slidably support the first linkage member and the second linkage member, and pivotably engaging the first peg and the second peg.

15. The articulation assembly according to claim 14, wherein the mount defines laterally spaced apart slots configured to slidably receive the first linkage member and the second linkage member in the spaced apart slots.

16. The articulation assembly according to claim 14, wherein the mount defines grooves laterally spaced apart, the grooves configured to pivotably support the first peg and the second peg of the articulation joint, respectively.

17. The articulation assembly according to claim 14, wherein the mount defines longitudinal bores spaced apart from a central axis defined by the mount, the longitudinal bores configured to slidably receive the first actuation member and the second actuation member.

18. The articulation assembly according to claim 14, wherein the first actuation member and the second actuation member include respective distal portions bendable to form an arcuate profile.

* * * * *